US00PP31457P2

(12) United States Plant Patent
Nebelmeir

(10) Patent No.: US PP31,457 P2
(45) Date of Patent: Feb. 18, 2020

(54) POINSETTIA PLANT NAMED 'LAZZPOSUGI'

(50) Latin Name: ***Euphorbia pulcherrima* Willd.**
Varietal Denomination: LAZZPOSUGI

(71) Applicant: Johannes Nebelmeir, Hann. Munden (DE)

(72) Inventor: Johannes Nebelmeir, Hann. Munden (DE)

(73) Assignee: LAZZERI SOCIETA AGRICOLA a.r.L., Sabaudia (IT)

( * ) Notice: Subject to any disclaimer, the term of this patent is extended or adjusted under 35 U.S.C. 154(b) by 0 days.

(21) Appl. No.: 16/350,929

(22) Filed: Feb. 1, 2019

(51) Int. Cl.
*A01H 5/02* (2018.01)
*A01H 6/38* (2018.01)

(52) U.S. Cl.
USPC ..... Plt./303
CPC ..... *A01H 6/38* (2018.05)

(58) Field of Classification Search
USPC ..... Plt./303
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of Poinsettia plant named 'LAZZPOSUGI', characterized by its broadly upright and uniformly mounding plant habit; moderately vigorous to vigorous growth habit; freely branching habit; dark green-colored leaves; relatively early flowering; large and full inflorescences with red and light yellow bi-colored flower bracts; and excellent post-production longevity.

2 Drawing Sheets

Botanical designation: *Euphorbia pulcherrima* Willd.
Cultivar denomination: 'LAZZPOSUGI'.

BACKGROUND OF THE INVENTION

The present invention relates to a new and distinct cultivar of Poinsettia plant, botanically known as *Euphorbia pulcherrima* Willd. and hereinafter referred to by the name 'LAZZPOSUGI'.

The new Poinsettia plant is a product of a planned breeding program conducted by the Inventor in Sabaudia, Italy. The objective of the breeding program is to create new uniform and freely-branching Poinsettia plants with attractive flower bracts.

The new Poinsettia plant is a naturally-occurring branch mutation of *Euphorbia pulcherrima* Willd. 'Superba Glitter Red & White', not patented. The new Poinsettia plant was discovered and selected by the Inventor on a single flowering plant of 'Superba Glitter Red & White' in a controlled greenhouse environment in Sabaudia, Italy in December, 2015.

Asexual reproduction of the new Poinsettia plant by terminal vegetative cuttings in a controlled greenhouse environment in Sabaudia, Italy since May, 2016 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'LAZZPOSUGI'. These characteristics in combination distinguish 'LAZZPOSUGI' as a new and distinct Poinsettia plant:

1. Broadly upright and uniformly mounding plant habit.
2. Moderately vigorous to vigorous growth habit.
3. Freely branching habit.
4. Dark green-colored leaves.
5. Relatively early flowering.
6. Large and full inflorescences with red and light yellow bi-colored flower bracts.
7. Excellent post-production longevity.

Plants of the new Poinsettia can be compared to plants of the mutation parent, 'Superba Glitter Red & White'. Plants of the new Poinsettia differ primarily from plants of 'Superba Glitter Red & White' in flower bract color as plants of the new Poinsettia have red and light yellow bi-colored flower bracts whereas plants of 'Superba Glitter Red & White' have pink, red and white tri-colored flower bracts.

Plants of the new Poinsettia can be compared to plants of *Euphorbia pulcherrima* Willd. 'Primero Glitter', not patented. In side-by-side comparisons, plants of the new Poinsettia differ primarily from plants of 'Primero Glitter' in the following characteristics:

1. Plants of the new Poinsettia have a more uniform plant habit than plants of 'Primero Glitter'.
2. Plants of the new Poinsettia flower about one to two weeks earlier than plants of 'Primero Glitter'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors ofthe new Poinsettia plant.

The photograph on the first sheet comprises a side perspective view of a typical flowering plant of 'LAZZPOSUGI' grown in a container.

The photograph on the second sheet is a close-up view of a typical inflorescence of 'LAZZPOSUGI'.

DETAILED BOTANICAL DESCRIPTION

The aforementioned photographs and following observations and measurements describe plants grown during the autumn and winter in 13-cm containers in a glass-covered greenhouse in Merano, Italy and under cultural practices typical of commercial Poinsettia production. During the production of the plants, day temperatures ranged from 15° C. to 20° C., night temperatures ranged from 10° C. to 15° C. and light levels ranged from 40 to 55 klux. Plants were pinched one time two weeks after planting, grown under natural daylength conditions and were five months old when the photographs and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'LAZZPOSUGI'.

Parentage: Naturally-occurring branch mutation of *Euphorbia pulcherrima* Willd. 'Superba Glitter Red & White', not patented.

Propagation:

*Type.*—Terminal vegetative cuttings.

*Time to initiate roots, summer.*—About two weeks at soil temperatures ranging from 22° C. to 25° C. and ambient temperatures ranging from 25° C. to 30° C.

*Time to produce a rooted young plant, summer.*—About 24 days at soil temperatures ranging from 22° C. to 25° C. and ambient temperatures ranging from 25° C. to 30° C.

*Root description.*—Medium to thick, slightly fleshy; typically pale creamy white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Broadly upright and uniformly mounded plant habit; inverted triangle with rounded crown; large and full inflorescences positioned above the foliar plane; moderately vigorous to vigorous growth habit and moderate to rapid growth rate.

*Plant height, soil level to top of floral plane.*—About 29 cm.

*Plant diameter or spread.*—About 50 cm.

*Lateral branch description.*—Branching habit: Freely branching habit with about five to seven lateral branches developing after pinching. Length: About 25 cm. Diameter: About 6 mm to 8 mm. Internode length: About 8 mm to 18 mm. Strength: Strong. Texture and luster: Smooth, glabrous; semi-glossy. Color: Close to 137B to 137C; with subsequent development, color becoming closer to 199A.

*Leaf description.*—Arrangement: Alternate, simple. Length: About 10 cm to 12 cm. Width: About 6 cm to 9 cm. Shape: Ovate. Apex: Acuminate. Base: Cuneate. Margin: Mostly entire with occasionally one to three shallow lobes; slightly undulate. Venation pattern: Pinnate, reticulate. Texture and luster, upper and lower surfaces: Smooth, glabrous; matte. Color: Developing leaves, upper surface: Close to 139A. Developing leaves, lower surface: Close to 147B. Fully expanded leaves, upper surface: Close to 139A; venation, close to 146B. Fully expanded leaves, lower surface: Close to 137B; venation, close to 146C.

*Petioles.*—Length: About 3 cm to 5 cm. Diameter: About 2.5 mm. Strength: Moderately strong. Texture and luster, upper and lower surfaces: Smooth, glabrous; semi-glossy. Color, upper surface: Close to 178A. Color, lower surface: Close to 178B.

Inflorescence description:

*Inflorescence type and habit.*—Large full inflorescences are compound corymbs of cyathia with colored flower bracts subtending the cyathia; one inflorescence per lateral branch with inflorescences positioned above and beyond the foliar plane.

*Fragrance.*—None detected.

*Natural flowering season.*—Plants flower naturally during the late autumn to winter under long nyctoperiod conditions; inflorescence initiation and development can be induced under artificial long nyctoperiod conditions; relatively early flowering, response time is about eight weeks.

*Post-production longevity.*—Excellent post-production longevity; plants of the new Poinsettia maintain good substance and bract color for about five to seven weeks; flower bracts persistent.

*Inflorescence width.*—About 22 cm to 26 cm.

*Inflorescence height.*—About 4 cm to 6 cm.

*Flower bracts.*—Quantity per inflorescence: About 15. Length: About 9.5 cm to 14 cm. Width: About 5.5 cm to 10.5 cm. Shape: Ovate. Apex: Acuminate. Base: Obtuse. Margin: Mostly entire or occasionally shallowly lobed; slightly undulate. Aspect: Horizontal to slightly drooping. Venation: Pinnate. Texture and luster, upper and lower surfaces: Moderately rugose, glabrous; matte. Color: Developing bracts, upper surface: Random and variable sectors, splotches and spots, close to 46B and 8D. Developing bracts, lower surface: Random and variable sectors, splotches and spots, close to 46C and 8D. Fully expanded bracts, upper surface: Random and variable sectors, splotches and spots, close to 46A and 8C; venation, close to 46A and 8C; colors becoming closer to 53B and 160C with development. Fully expanded bracts, lower surface: Random and variable sectors, splotches and spots, close to 45D and 8C; venation, close to 45D and 8C; colors becoming closer to 53B and 160C with development. Bract petioles: Length: About 2.8 cm. Diameter: About 2.5 mm. Texture and luster, upper and lower surfaces: Smooth, glabrous; semi-glossy. Color, upper surface: Close to 184A. Color, lower surface: Close to 181A.

*Cyathia.*—Quantity per corymb: About six to eight. Length: About 8 mm. Width: About 6 mm. Shape: Ovoid to spherical. Texture and luster, inner and outer surfaces: Smooth, glabrous; matte. Color, developing, inner and outer surfaces: Close to 144A. Color, fully developed, inner surface: Close to 144D. Color, fully developed, outer surface: Close to 144C. Nectaries: Quantity per cyathium: Typically one or two. Length: About 5 mm. Diameter: About 3 mm. Shape: Lip-shaped. Texture and luster, inner and outer surfaces: Smooth, glabrous; matte. Color, fully developed, inner surface: Close to 12A. Color, fully developed, outer surface: Close to 9B.

*Pedicels.*—Length: About 1 mm to 3 mm. Diameter: About 1.5 mm. Strength: Moderately strong. Texture and luster: Smooth, glabrous; semi-glossy. Color: Close to 144B.

*Reproductive organs.*—Stamens: To date, stamen development has not been observed on plants of the new Poinsettia. Pistils: Quantity per cyathia: Typically three. Pistil length: About 2 mm to 3 mm. Style length: About 2 mm to 3 mm. Style shape: Recurved. Fruits: Quantity: None to very few with one to three seeds. Length: About 8 mm to 12 mm. Diameter: About 6 mm to 10 mm. Texture: Smooth, glabrous.

Pathogen & pest resistance: To date, plants of the new Poinsettia have not been shown to be resistant to pathogens and pests common to Poinsettia plants.

It is claimed:

1. A new and distinct Poinsettia plant named 'LAZZPOSUGI' as illustrated and described.

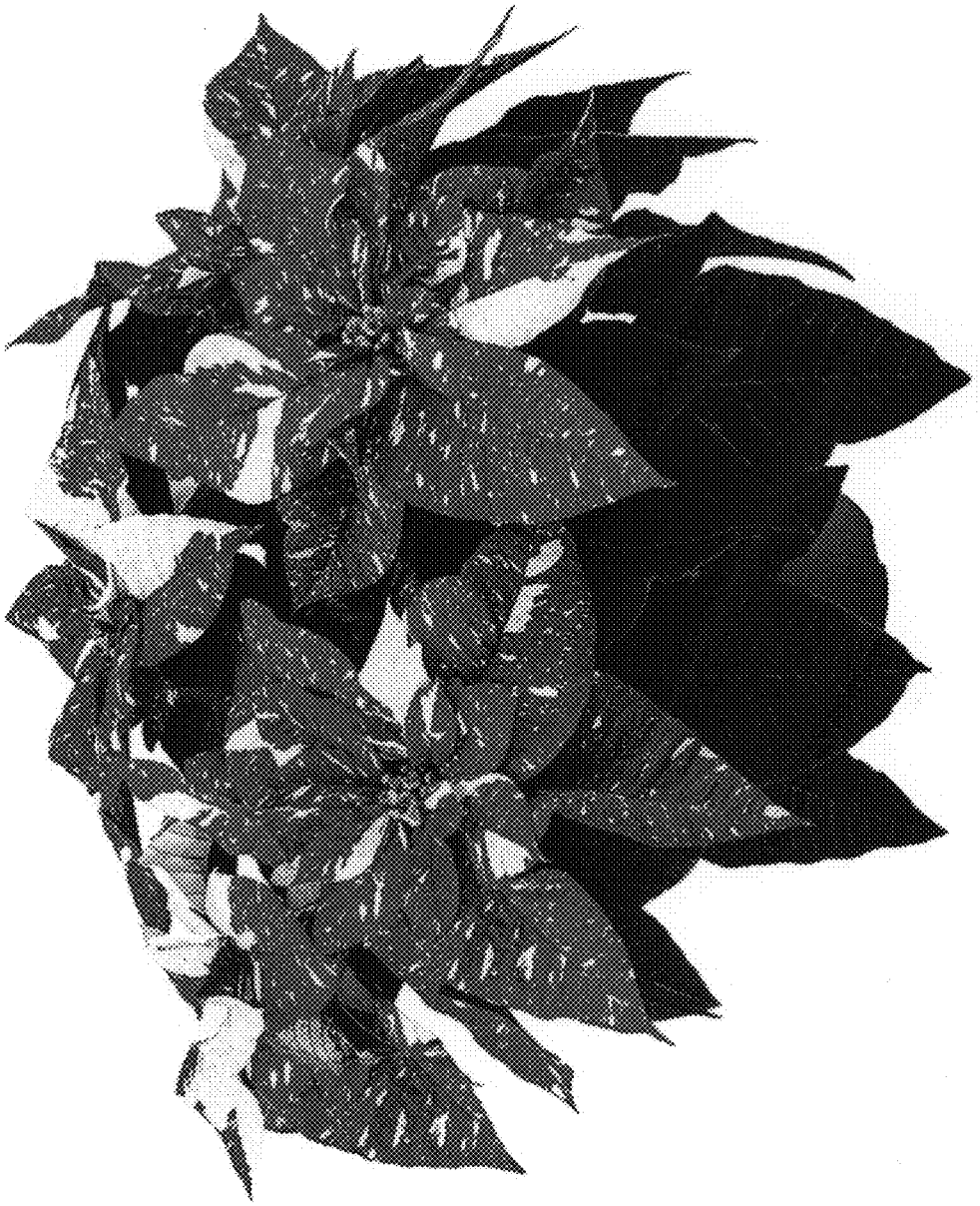

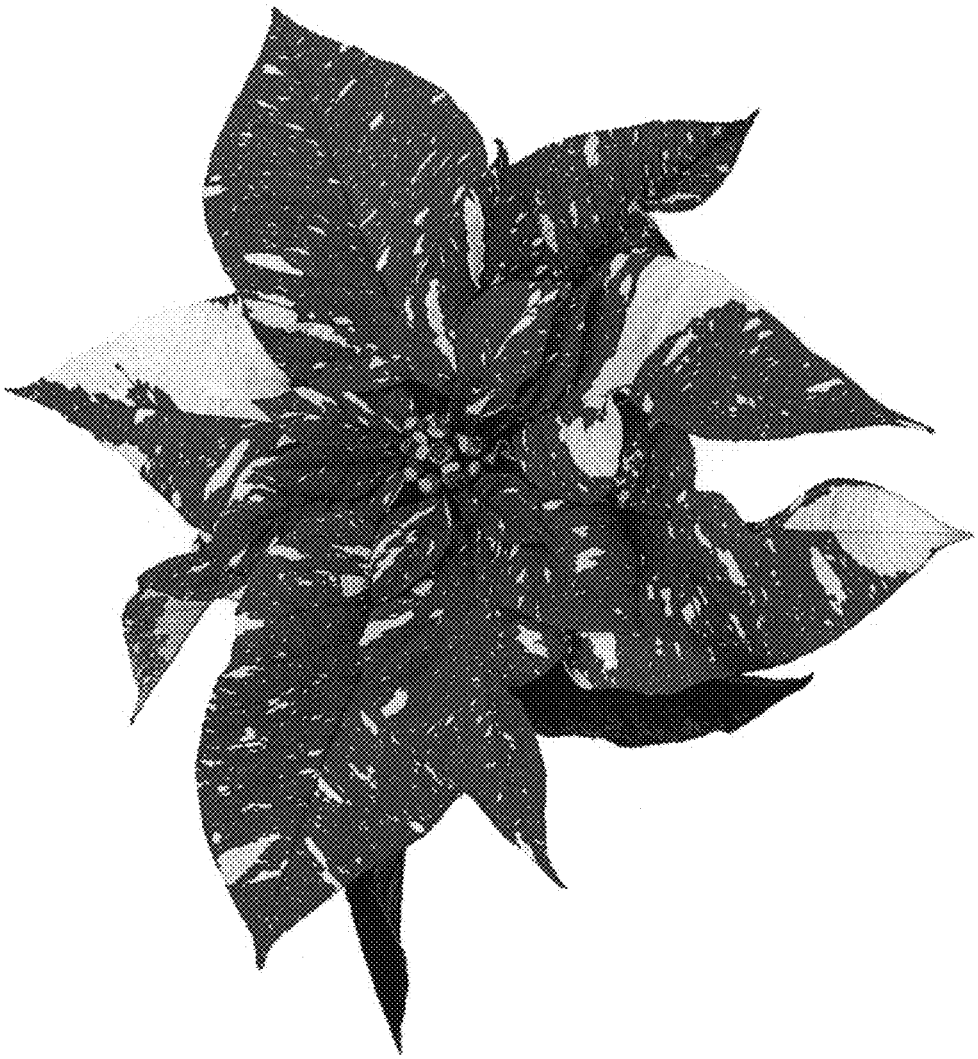

* * * * *